(12) United States Patent
Williams

(10) Patent No.: US 7,657,325 B2
(45) Date of Patent: Feb. 2, 2010

(54) IMPLANTABLE MEDICAL LEAD INCLUDING A HELICAL FIXATION MEMBER

(75) Inventor: Terrell M. Williams, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 527 days.

(21) Appl. No.: 11/323,016

(22) Filed: Dec. 30, 2005

(65) Prior Publication Data
US 2007/0156218 A1 Jul. 5, 2007

(51) Int. Cl.
*A61N 1/05* (2006.01)
(52) U.S. Cl. .................. 607/127; 607/115
(58) Field of Classification Search ............ 607/126, 607/127, 131
See application file for complete search history.

(56) References Cited

U.S. PATENT DOCUMENTS

| | | | |
|---|---|---|---|
| 5,456,708 A | * | 10/1995 | Doan et al. ............ 607/127 |
| 5,522,876 A | | 6/1996 | Rusink |
| 5,551,427 A | * | 9/1996 | Altman ............... 600/374 |
| 5,658,327 A | * | 8/1997 | Altman et al. ........... 607/127 |
| 6,144,866 A | | 11/2000 | Miesel et al. |
| 6,493,591 B1 | | 12/2002 | Stokes |
| 2002/0161423 A1 | | 10/2002 | Lokhoff et al. |
| 2003/0114907 A1 | * | 6/2003 | Laabs et al. .............. 607/126 |
| 2004/0068299 A1 | | 4/2004 | Laske et al. |
| 2004/0102830 A1 | | 5/2004 | Williams |
| 2005/0085886 A1 | | 4/2005 | Hess et al. |

FOREIGN PATENT DOCUMENTS

| | | |
|---|---|---|
| EP | 1595572 A | 11/2005 |
| WO | WO2005037368 A | 4/2005 |
| WO | WO2006060760 A | 6/2006 |

* cited by examiner

*Primary Examiner*—Carl H Layno
*Assistant Examiner*—Brian T Gedeon
(74) *Attorney, Agent, or Firm*—Carol F. Barry

(57) ABSTRACT

An implantable medical lead comprises an elongated body extending between a proximal end and a distal end, and a helical fixation member extending from the distal end of the elongated body. The helical fixation member is configured to fix the implantable medical lead at an implant site and includes a tip comprising a first surface generally facing a center axis of the helical fixation member.

20 Claims, 4 Drawing Sheets

IMPLANTABLE MEDICAL LEAD INCLUDING A HELICAL FIXATION MEMBER

BACKGROUND OF THE INVENTION

The present invention relates generally to the field of implantable medical devices, and more particularly to a helical fixation member including a tip comprising a first surface that generally faces a center axis of the helical fixation member.

Implantable medical leads are used with a wide variety of medical devices to provide electrical and/or mechanical connections between the device and a location within a body. For example, implantable medical leads are commonly used with pacemakers, cardioverters, and defibrillators to provide an electrical connection between the device and an electrode positioned within or adjacent to the heart. Recently becoming more prevalent are implantable medical leads that are configured to advance from the right atrium of the heart, through the coronary sinus, and into a cardiac vein for sensing electrical activity in or providing electrical stimulation to the left ventricle of the heart. Advancing from the right atrium to the left ventricle is one of several applications that require fixation of an implantable medical lead parallel to endocardial surfaces.

For many applications, it is preferred that placement of the lead be fixed. One mechanism for actively fixing an implantable medical lead includes an electrode that is configured to wedge in cardiac tissue.

SUMMARY OF THE INVENTION

The present invention is an implantable medical lead including a helical fixation member for actively fixing the implantable medical lead at a desired implant site. The helical fixation member includes a center axis and a tip with a first surface that generally faces the center axis. The orientation of the first surface of the tip facilitates the introduction of the tip into the desired implant site.

DETAILED DESCRIPTION

Figure 1:
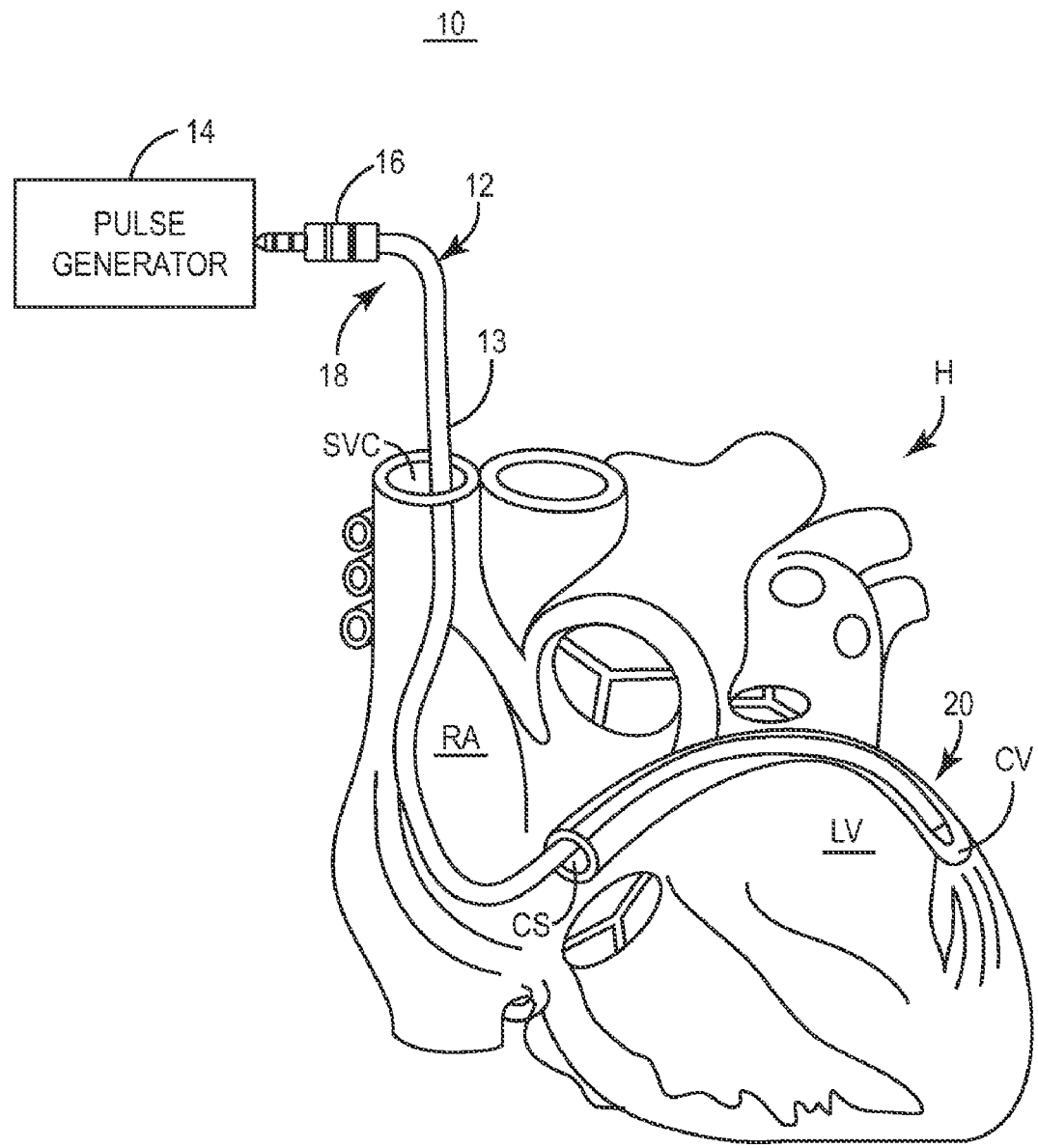
FIG. 1 is a schematic diagram of an implantable medical device incorporating an implantable medical lead in accordance with the present invention.

An implantable medical lead in accordance with the present invention is suitable for electrically and/or a mechanically connecting an implantable medical device (IMD) with a location within the vasculature of the body. FIG. 1 is a schematic diagram of IMD 10 incorporating implantable medical lead 12 in accordance with the present invention. IMD 10 includes pulse generator 14, which may be a cardiac pacemaker or a cardioverter/defibrillator, for sensing electrical activity in heart H and providing therapy. Alternatively, lead 12 may be used with any type of medical device that requires an electrical and/or a mechanical connection to a location within the vasculature of the body, such as a sensing device or a drug pump for administering a pharmaceutical, biologic or genetic agent.

Lead 12 includes elongated body 13 extending between proximal end 18 and distal end 20. Elongated body 13 is preferably formed of a biocompatible plastic such as polyurethane or silicone rubber. Elongated body 13 functions as an insulating sleeve in which many of the electrical and mechanical elements of lead 12 are protected. Connector assembly 16 is connected to proximal end 18 of elongated body 13 and couples lead 12 to pulse generator 14, as is well known in the art.

In the application of lead 12 shown in FIG. 1, lead 12 extends from pulse generator 14, through superior vena cava SVC into right atrium RA of heart H, and then through coronary sinus CS into cardiac vein CV. As described in greater detail below, medical lead 12 includes an active fixation member (i.e., helical fixation member 30) in accordance with the present invention at distal end 20 to facilitate the fixation of distal end 20 at an implant site within cardiac vein CV. The implant site is in a plane generally parallel to longitudinal axis 22 (shown in FIG. 2) of elongated body 13 of lead 12. Of course, in alternate embodiments, distal end 20 of lead 12 can also be fixed to other implant sites within a patient, which are determined by the intended function of the medical device to which lead 12 is coupled.

The active fixation member may double as an electrode that is fixed to a left ventricular epicardial site of heart H for sensing electrical activity in and providing electrical stimulation to left ventricle LV of heart H. Lead 12 may also include physiological sensors for gathering physiological data. If lead 12 is used for administering a pharmaceutical, biologic or genetic agent, lead 12 may include a fluid delivery lumen coupled to helical fixation member 30. Devices that integrate monitoring and therapy delivery features with implantable medical leads are well known in the art.

Figure 2:
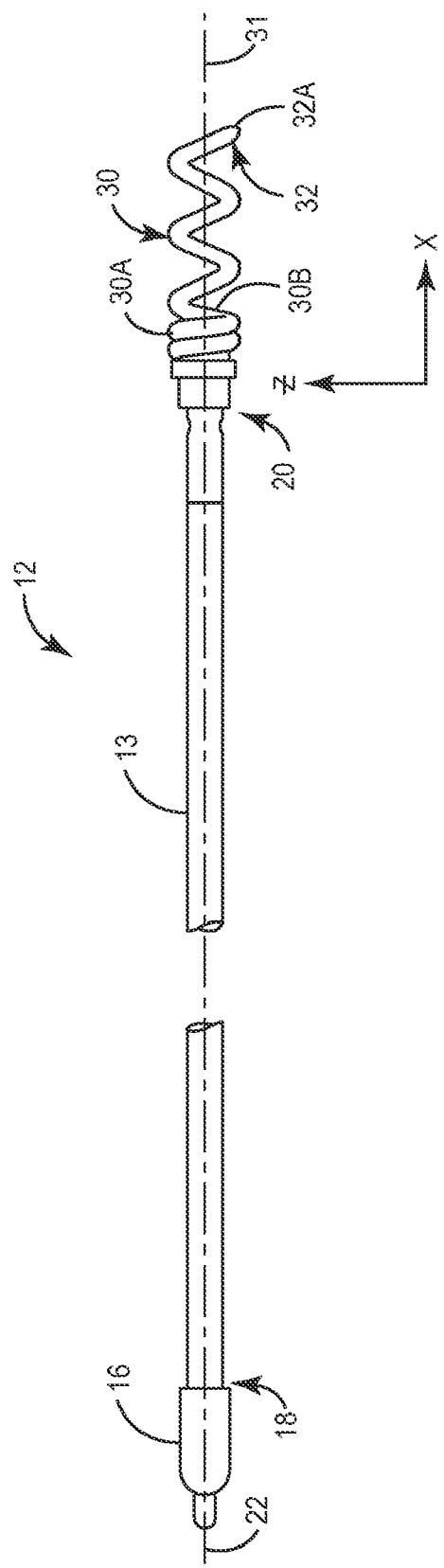
FIG. 2 is a plan view of the inventive implantable medical lead of FIG. 1, which illustrates a helical fixation member extending from a distal end of the implantable medical lead.

FIG. 2 is a plan view of implantable medical lead 12 of FIG. 1. Lead 12 includes elongated body 13 extending between proximal end 18 and distal end 20 along longitudinal axis 22, which is an imaginary line running through a center of elongated body 13 along an x-axis direction (orthogonal x-z axes are provided in FIG. 2). Connector assembly 16 is positioned at proximal end 18 of elongated body 13, while helical fixation member 30 extends from distal end 20 of elongated body 13.

Helical fixation member 30 actively fixes distal end 20 of elongated body 12 at a desired implant site. Helical fixation member 30 doubles as an electrode to which pacing pulses may be delivered and through which cardiac electrical function can be sensed by pulse generator 14. Materials for forming helical fixation member 30 include, but are not limited to, platinum, iridium, titanium, nickel alloys, and platinum-iridium alloys (e.g., about 70 to about 90 weight percent of platinum and about 10 to about 30 weight percent of iridium). In alternate embodiments where helical fixation member 30 does not function as an electrode (e.g., where lead 12 is used only to deliver a therapeutic agent to a desired location within the vasculature), materials for forming helical fixation member 30 may further include without limitation polycarbonate, polypropylene, synthetic resins and super-elastic materials, such as Nitinol.

In the embodiment shown in FIG. 2, helical fixation member 30 is comprised of multiple turns that are concentric about center axis 31, which is aligned with longitudinal axis 22 of elongated body 13. Helical fixation member 30 winds around center axis 31 in a counterclockwise direction, thereby defining outer surface 30A and inner surface 30B. Outer surface 30A is configured to engage with a catheter, which may be used to guide lead 12 to the desired implant site. Inner surface 30B faces center axis 31 and is configured to engage with a guide wire, which may be used to guide lead 12 to the implant site. As known in the art, the guide wire may be used in addition to or instead of the catheter.

Helical fixation member 30 is configured to fix distal end 20 of elongated body 13 at a desired implant site. In order to accomplish this, helical fixation member 30 includes a tissue-piercing tip 32, which is described in further detail in reference to FIGS. 3-7. Tip 32 may be referred to as a "chisel-tip" because of its shape. In order to fix distal end 20 of lead 12 at a desired implant site, helical fixation member 30 is positioned at the desired implant site and rotated to "screw" tip 32 and one or more turns of helical fixation member 30 into the desired implant site, which may be, for example, cardiac vasculature. Mechanisms for moving helical fixation member 30 are well known to those skilled in the art, but are typically activated by a rotating a connector pin that is located at proximal end 18 of lead 12. Tip 32 includes a sharp edge 32A, which is used to facilitate the introduction of tip 32 into the desired implant site. While the remainder of the description below refers to cardiac vasculature or tissue and an implant site interchangeably, it should be understood that implantable medical lead 12 in accordance with the present invention is also suitable for use with other implant sites within a body.

In general, the shape and location of tip 32 of helical fixation member 30 with respect to center axis 31 and outer surface 30A of helical fixation member 30 contribute to the ability of tip 32 to sufficiently pierce through cardiac tissue to implant lead 12. More specifically, the shape and location of tip 32 may affect the direction and force with which tip 32 contacts an implant site. Tip 32 in accordance with the present invention expands the possible applications of lead 12.

Recent years have seen medical devices become more advanced and complex, requiring new medical lead configurations to facilitate fixation of elongated medical devices at targeted implant sites within a patient. The new developments have resulted in more applications that require a fixation mechanism to penetrate through a relatively hard (or tough) implant site, such as a His bundle, which may be the desired implant site for a type of pacing known as "His bundle pacing." New developments have also resulted in more applications in which lead 12 is affixed to an implant site that is substantially parallel to longitudinal axis 22 of elongated body 13. In addition to being a dynamic environment, some cardiac tissues present tortuous planes, making standard screw-in attachments impractical or difficult to use. Substantially parallel implant sites frequently occur, for example, when lead 12 is implanted in left ventricle LV of heart H (shown in FIG. 1) or in an outflow tract of right ventricle RV of heart H.

Lead 12 incorporating helical fixation member 30 in accordance with the present invention addresses the aforementioned issues that have recently arisen. As described in detail below, design of tip 32 of helical fixation member 30 is configured to fix lead 12 at an implant site that is substantially parallel to longitudinal axis 22 of elongated body 13. Of course, tip 32 may also be used to fix lead 12 at other implant sites, such as implant sites that are substantially perpendicular to longitudinal axis 22 of elongated body 13. Further, the design of tip 32 also facilitates the entry of tip 32 into relatively hard fibrotic tissue. A lead 12 in accordance with the present invention is suitable for use in conjunction with His bundle pacing because of the ability of tip 32 to penetrate relatively hard fibrotic tissue. Furthermore, in a dynamic environment such as the heart, lead 12 of the present invention enables a quick pierce and attachment on a moving tissue that is oriented in a non-perpendicular plane to tip 32.

Figure 3:
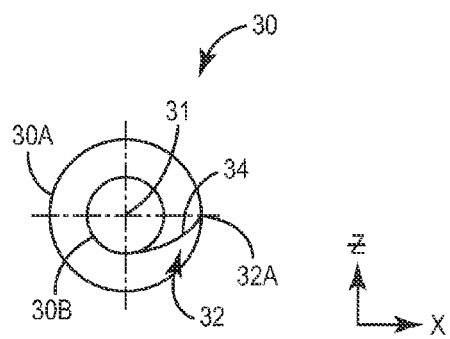
FIG. 3 is an end view of the helical fixation member of FIG. 2, which is concentric about a center axis.

FIG. 3 illustrates an end view of helical fixation member 30, which is concentric about center axis 31 (which is substantially perpendicular to the plane of the image of FIG. 3). Helical fixation member 30 includes tip 32 with sharp end 32A and first surface 34. First surface 34 of tip 32 generally faces center axis 31 of helical fixation member 30 and, together with outer surface 30A of helical fixation member 30, helps to define sharp end 32A of tip 32. Sharp end 32A of tip 32 helps to introduce helical fixation member 30 into the implant site by providing a sharp edge with which to pierce through the tissue at the implant site. Furthermore, it has been found that when first surface 34 faces center axis 31 of helical fixation member 30, the shape of tip 32 enables helical fixation member 30 to engage with (and thereby fix lead 12) an implant site that is substantially parallel to longitudinal axis 22. It has also been found that when tip 32 includes first surface 34 that generally faces center axis 31, tip 32 is able to penetrate through relatively hard implant tissue, such as the central fibrous tissue surrounding the His bundle.

In order to help prevent tip 32 of helical fixation member 30 from prematurely penetrating tissue prior to reaching the implant site, tip 32 is configured such that first surface 34 is positioned along inner surface 30B of helical fixation member 30. This configuration enables sharp edge 32A of tip 32 to penetrate tissue only after helical fixation member 30 is rotated (in a counterclockwise direction for the embodiment shown in FIG. 3). Furthermore, if a guide wire is positioned within helical fixation member 30 (where inner surface 30B engages the guide wire), a distal end of the guide wire leads the first surface 34 and sharp edge 32A through the vasculature, which also protects surrounding tissue from sharp edge 32A of tip 32.

Figure 4:
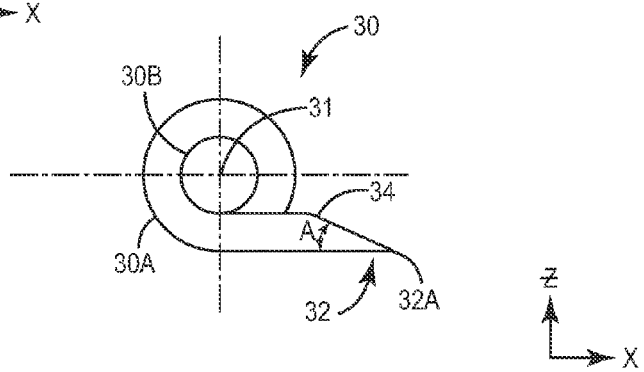
FIG. 4 is the end view of helical fixation member of FIG. 3, where the tip of the helical fixation member has been unwound.

FIG. 4 is the end view of helical fixation member 30 of FIG. 3, where tip 32 of helical fixation member 30 has been unwound. In the embodiment shown in FIG. 4, first surface 34 is substantially planar. First surface 34 is formed by cutting tip 32 along a plane that is substantially parallel to central axis 31, which results in first surface 34 that generally faces center axis 31 of helical fixation member 30 when tip 32 is wound (as shown in FIG. 3). First surface 34 is oriented at angle A with respect to outer surface 30A of helical fixation member 30. Angle A is any suitable angle, which may be modified to accommodate different applications of lead 12 (shown in FIG. 2).

Figure 5A:
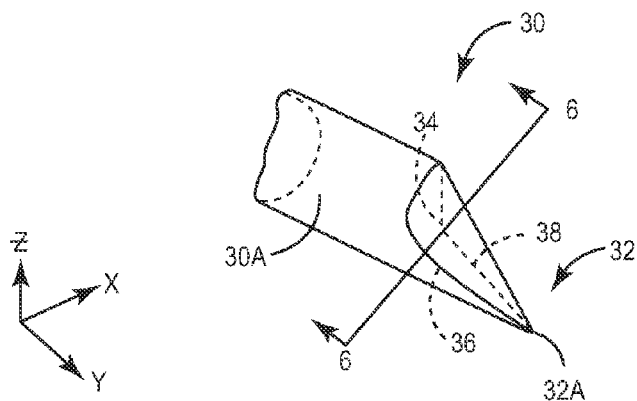
FIG. 5A is a partial perspective view of the partially unwound helical fixation member of FIG. 4 showing tip shapes.

FIG. 5A is a partial perspective view of the partially unwound helical fixation member 30 of FIG. 4. As FIG. 5 illustrates, in one embodiment, tip 32 also includes second surface 36 oriented at an angle with respect to first surface 34. First and second surfaces 34 and 36, respectively, intersect to define apex 38, which provides a sharp edge or ridge to facilitate the introduction of tip 32 of helical fixation member 30 into the tissue at an implant site. When helical fixation member 30 is wound (as shown in FIG. 2), apex 38 is positioned along inner surface 30B (shown in FIGS. 3-4) of helical fixation member 30 and second surface 36 is positioned between turns of helical fixation member 30.

Figure 5B:
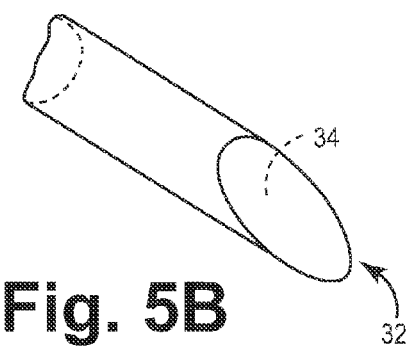
FIG. 5B is a partial perspective view of the partially unwound helical fixation member of FIG. 4 showing a tip shape.

FIG. 5B is an alternate embodiment of the present invention showing a single surface that defines a piercing apex of helical member 30.

Referring to FIG. 5A, tip 32 is configured to prevent sharp end 32A and apex 38 from prematurely fixing lead 12 prior to reaching the desired implant site. Specifically, sharp end 32A and apex 38 are the features of tip 32 that are likely to first engage with the desired implant site, and by positioning sharp end 32A and apex 38 along an inner surface 30B of helical fixation member 30, sharp end 32A and apex 38 are less likely to "snag" on a surrounding structure. If a delivery catheter is used to guide implantable medical lead 12 (shown in FIG. 2) to the implant site, the catheter engages with round outer surface 30A of helical fixation member because apex 38 and sharp end 32A are positioned along inner surface 30B of helical fixation member 30. As a result, positioning apex 38 along inner surface 30B of helical fixation member also helps to prevent apex 38 (as well as sharp end 32A) from scraping material from the inside of a delivery catheter.

Figure 6:
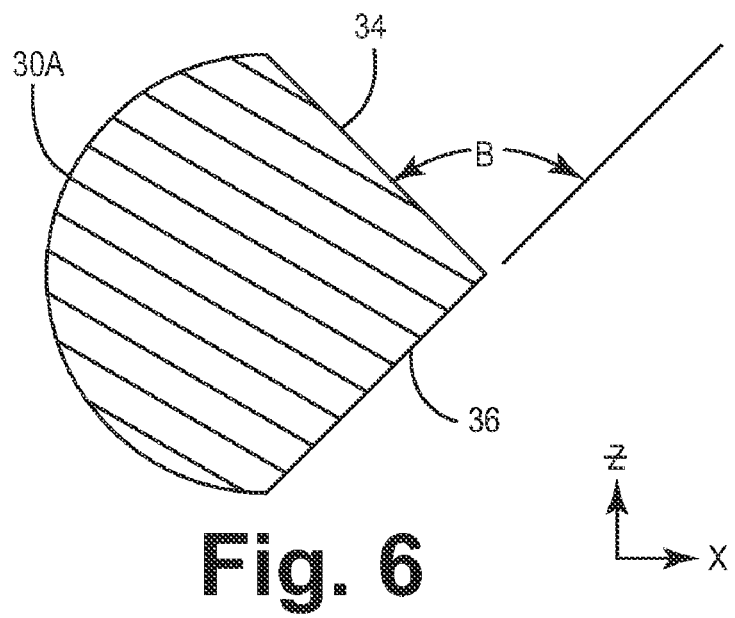
FIG. 6 is a sectional view of the tip of the helical fixation member of FIG. 5 taken along line 6-6 in FIG. 5.

Further referring to FIG. 5A, the angular relationship between first surface 34 and second surface 36 is illustrated in FIG. 6, which is a cross-sectional view of tip 32 of helical fixation member 30 taken along line 6-6 in FIG. 5A. In FIG. 6, substantially planar first and second surfaces 34 and 36, respectively, are oriented at angle B with respect to each other. In the embodiment of tip 32 shown in FIG. 6, angle B is preferably less than about 180°. In one particular embodiment, angle B is about 90°.

As with the other angular dimensions provided above, one skilled in the art may modify angle B without departing from the scope of the present invention.

Figure 7:
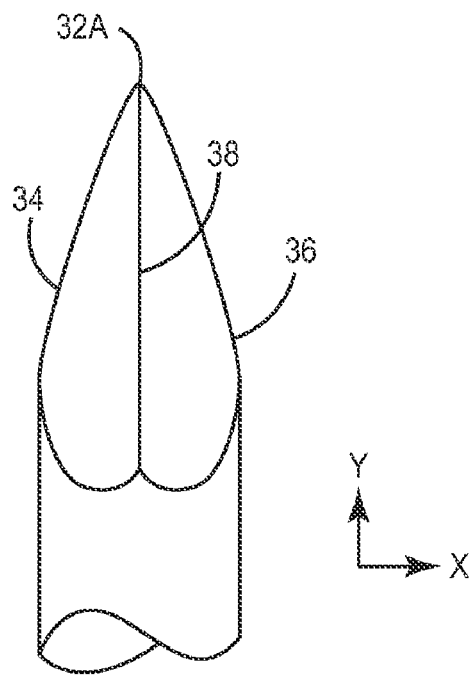
FIG. 7 is a plan view of the tip of the helical fixation member of FIGS. 5-6, and shows an apex that is defined by the intersection of a first surface and a second surface of the tip.

FIG. 7 is a plan view of tip 32 of helical fixation member 30 and shows apex 38 converging with sharp end 32A of tip 32. As FIG. 7 shows, first and second surfaces 34 and 36, respectively, are substantially equal in area when angle B between first and second surfaces 34 and 36, respectively, is about 90°. In applications in which helical fixation member 30 is used to deliver fluid, helical fixation member 30 may be hollow. One skilled in the art will recognize that in those applications, first and second surfaces 34 and 36, respectively, may not be solid surfaces, as FIGS. 5-7 illustrate.

In one method of forming tip 32 of helical fixation member 30 in accordance with the present invention, material wound around a center axis (e.g., center axis 31) to form a helical body, as known in the art. One end (i.e., tip 32) of the helical body is then ground along a first plane to form first surface 34, where the first plane faces center axis 31 (e.g., the first plane may be substantially parallel to center axis 31). Thereafter, tip 32 is ground along a second plane to form second surface 36, which is oriented at angle B from first surface 34. Alternatively, second surface 36 may be formed before first surface 34. Helical fixation member 30 may then be coated with titanium nitride for corrosion resistance. Other suitable methods of forming tip 32 are also contemplated. For example, in an alternate method of forming helical fixation member 30, first and second surfaces 34 and 36, respectively, may be formed at one end of a length of material prior to forming a helical body with the material.

Although the present invention has been described with reference to preferred embodiments, workers skilled in the art will recognize that changes may be made in form and detail without departing from the spirit and scope of the invention.

The invention claimed is:

1. An implantable medical lead comprising:
an elongated body extending between a proximal end and a distal end; and
a helical fixation member configured to fix the implantable medical lead at an implant site and extending from the distal end of the elongated body,
the helical fixation member having windings with a circumference that is concentric about a center axis,
the helical member defining an inner surface and an outer surface,
the helical fixation member terminating in an end winding that is cross cut from the inner surface to the outer surface to form a tissue-piercing distal tip, the tip being configured with a single facet defined by a first cut surface positioned along the inner surface of the end winding, and wherein the tip is configured to have a round surface along the outer surface opposite the first cut single facet surface.

2. The implantable medical lead of claim 1,
wherein the tip of the helical fixation member is further configured to have a second cut surface positioned along the inner surface,
wherein an apex is defined by an intersection of the first cut surface and the second cut surface; and
wherein the tip of the helical fixation member is configured to have a round surface along the outer surface opposite the first cut surface and the second cut surface.

3. The implantable medical lead of claim 2, wherein the second cut surface is oriented at an angle of less than about 180° with respect to the first cut surface.

4. The implantable medical lead of claim 3, wherein the angle is about 90°.

5. The implantable medical lead of claim 1, and further comprising:
a connector assembly connected to the proximal end of the elongated body, the connector assembly being configured to couple the implantable medical lead to an implantable medical device.

6. The implantable medical lead of claim 1, wherein the first cut surface extends approximately 90 degrees around the circumference of the helical fixation member.

7. The implantable medical lead of claim 1, wherein the inner surface of the helical fixation member is configured to engage a guide wire.

8. The implantable medical lead of claim 1, wherein the outer surface of the helical fixation member is configured to engage a catheter.

9. The implantable medical lead of claim 1, wherein the helical fixation member is configured for implant in cardiac tissue.

10. The implantable medical lead of claim 1, wherein the tip of the helical fixation member is configured to engage with an implant site that is substantially parallel to a longitudinal axis of the elongated body.

11. The implantable medical lead of claim 1, wherein the helical fixation member is at least partially formed of a material selected from a group consisting of: platinum, iridium, titanium, nickel alloy, platinum-iridium alloys, polycarbonate, polypropylene, synthetic resin, and a super-elastic material.

12. The implantable medical lead of claim 1, wherein the helical fixation member is an electrode.

13. The implantable medical lead of claim 1, wherein the implantable medical lead is a part of a system selected from a group consisting of: a fluid delivery system, a cardiac signal sensing system, a stimulation therapy system, and a neurostimulation system.

14. An active fixation member configured for use with an implantable medical device, the active fixation member comprising:
    a helical body including a distal end and winding in a first direction to define an outer surface and an inner surface, the helical body terminating in an end winding that is cross cut from the inner surface to the outer surface to form a tissue-piercing, chisel distal tip, the tip being configured with a single facet defined by a first cut surface positioned along the inner surface of the end winding, and wherein the tip is configured to have a round surface along the outer surface opposite the first cut single facet surface.

15. The active fixation member of claim 14, wherein the tissue-piercing tip further comprises:
    a second cut surface oriented at an angle of less than about 180° with respect to the first cut surface.

16. The active fixation member of claim 15, wherein the angle is about 90°.

17. The active fixation member of claim 14, wherein the helical body winds around a center axis and the tissue-piercing tip is configured to engage with an implant site that is substantially parallel to the center axis of the helical body.

18. A method of forming a helical fixation member including a center axis, the method comprising:
    winding a body around a center axis to form a helical body terminating in an end winding having an inner surface and an outer surface;
    cross-cutting the end winding along a first cut plane from the inner surface to the outer surface to form a tissue-piercing distal tip configured with a single facet defined by a first cut surface positioned along the inner surface of the end winding, and wherein the tip is configured to have a round surface along the outer surface opposite the first cut single facet surface.

19. The method of claim 18, wherein the end winding is cut along a first cut plane that is generally parallel to the center axis.

20. The method of claim 18, and further comprising:
    cutting the end winding of the helical body along a second cut plane oriented at an angle of less than about 180° with respect to the first cut plane.

\* \* \* \* \*

UNITED STATES PATENT AND TRADEMARK OFFICE
CERTIFICATE OF CORRECTION

| | | |
|---|---|---|
| PATENT NO. | : 7,657,325 B2 | Page 1 of 1 |
| APPLICATION NO. | : 11/323016 | |
| DATED | : February 2, 2010 | |
| INVENTOR(S) | : Terrell M. Williams | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 602 days.

Signed and Sealed this

Thirtieth Day of November, 2010

David J. Kappos
*Director of the United States Patent and Trademark Office*